United States Patent [19]

Ogahara et al.

[11] 4,146,731

[45] Mar. 27, 1979

[54] PROCESS FOR PREPARING GLYOXYLIC ACID

[75] Inventors: Junzo Ogahara, Ogaki; Kunihiko Sekiyama, Kashihara, both of Japan

[73] Assignee: Nippon Gohsei Kagaku Kogyo Kabushiki Kaisha, Osaka, Japan

[21] Appl. No.: 776,425

[22] Filed: Mar. 10, 1977

[30] Foreign Application Priority Data

Nov. 25, 1976 [JP] Japan .............................. 51-141875

[51] Int. Cl.² ............................................. C07C 51/26
[52] U.S. Cl. ................................. 562/531; 204/180 P
[58] Field of Search ...................... 260/530 R; 562/531

[56] References Cited

U.S. PATENT DOCUMENTS 3,281,460   10/1966   Gandon ........................... 260/530 R

FOREIGN PATENT DOCUMENTS 932369   8/1955   Fed. Rep. of Germany ...... 260/530 R

*Primary Examiner*—Vivian Garner
*Attorney, Agent, or Firm*—Armstrong, Nikaido, Marmelstein & Kubovcik

[57] ABSTRACT

Improved process for preparing glyoxylic acid by oxidizing glyoxal with nitric acid at a concentration of 4 to 10% by weight of nitric acid based on the weight of the reaction system, introducing oxygen or oxygen-containing gas into the reaction system so as to satisfy a relation $K_L a \cdot P \geq 150$, wherein $K_L a$ is a liquid-phase over-all mass transfer coefficient of the reactor (1/hour) and P is a partial pressure of oxygen in the reaction system (kg./cm.²). Glyoxylic acid can be prepared in high yields with less consumption of nitric acid and the generation of nitrogen oxides can be remarkably decreased.

5 Claims, 1 Drawing Figure

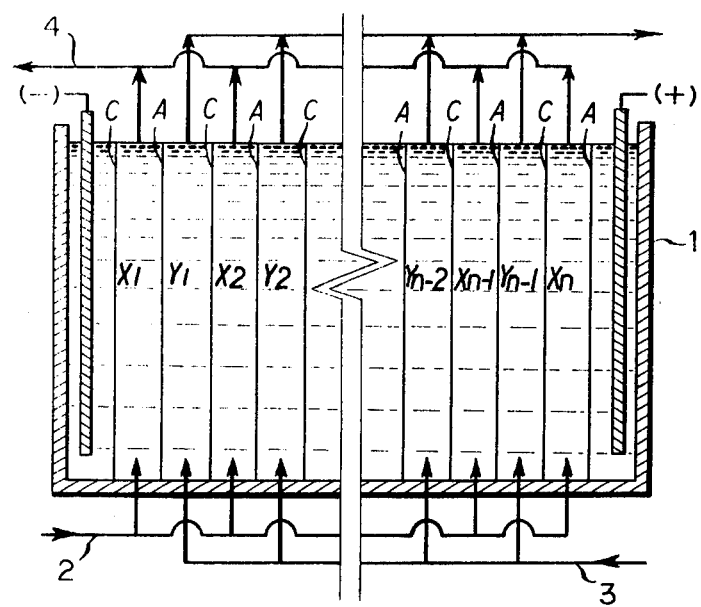

PROCESS FOR PREPARING GLYOXYLIC ACID

BACKGROUND OF THE INVENTION

The present invention relates to a process for preparing glyoxylic acid, and more particularly to an improved process for preparing glyoxylic acid by oxidizing glyoxal with nitric acid under particular conditions.

Glyoxylic acid has been commercially produced by oxidizing glyoxal with nitric acid in the presence or absence of sodium nitrite. According to this method, the yield of the glyoxylic acid to the consumed glyoxal is at most 60 to 75% by mole and carbon dioxide and organic acids such as oxalic acid are by-produced in large quantities. Further, a large quantity of nitric acid is consumed in the reaction, for instance, about 0.6 to 0.8 mole of nitric acid per mole of consumed glyoxal, and as a result, a large quantity of nitrogen oxides NOx generates.

OBJECTS OF THE INVENTION

It is an object of the present invention to provide an improved process for preparing glyoxylic acid by oxidizing glyoxal with nitric acid.

A further object of the invention is to provide a process for preparing glyoxylic acid from glyoxal in high yields.

A still further object of the invention is to reduce the consumption of nitric acid and the amount of the by-produced nitrogen oxides as compared with a conventional process.

These and other objects of the invention will become apparent from the description hereinafter.

BRIEF DESCRIPTION OF THE DRAWING

The single FIGURE is a schematic section view of an electrodialysis apparatus which may be employed in the present invention.

DETAILED DESCRIPTION

It has now been found that the above-mentioned objects can be accomplished by oxidizing glyoxal with nitric acid (1) at a concentration of 4 to 10% by weight of nitric acid based on the total weight of the reaction system, (2) introducing oxygen or an oxygen-containing gas into the reaction system, and (3) maintaining a condition satisfying a relation $K_L a \cdot P \geq 150$ wherein $K_L a$ is a liquid-phase over-all mass transfer coefficient of the reactor (1/hour) and P is a partial pressure of oxygen in the reaction system (kg./cm.$^2$). According to the process of the present invention, glyoxylic acid can be efficiently produced. For instance, the glyoxylic acid yield is over 90%, and the consumption of nitric acid and the generation of nitrogen oxides are remarkably decreased to respectively 1/15 and 1/60 time those in a conventional process. Also, when the obtained reaction mixture is subjected to electrodialysis, pure glyoxylic acid of which nitric acid content is very small can be efficiently obtained.

The above-mentioned effects of the present invention can be obtained only when the oxidation of glyoxal is conducted under the combination of the above conditions (1), (2) and (3).

It is important to maintain the nitric acid concentration during the reaction at 4 to 10% by weight, preferably at 5 to 8% by weight, based on the total weight of the reaction system. Since the concentration of nitric acid in the reaction system gradually drops with the progress of the reaction due to decomposition and consumption, it is necessary to add continuously or at intervals nitric acid to the reaction system during the reaction so as to maintain the concentration within the above range. When the concentration of nitric acid is less than 4% by weight, the yields of glyoxylic acid are low and the consumption of nitric acid and the generation of nitrogen oxides increase. Also, the reaction at a concentration of more than 10% by weight is not preferable, since the reaction control becomes difficult due to violent reaction and the removal of residual nitric acid from the obtained glyoxylic acid becomes also difficult.

In the process of the present invention, the reaction is carried out in the presence of a specific amount of oxygen, and it is necessary to introduce oxygen into the reaction system continuously or at intervals from the beginning of the reaction. When oxygen is not introduced like a conventional process, the effects of the present invention cannot be obtained. Even if air is present in a space of a reaction apparatus at the beginning of the reaction, such a small amount of oxygen is immediately discharged outside the reaction system by a by-produced gas. In the present invention, air or a mixture of oxygen gas with an inert gas can be employed as well as oxygen gas alone.

When the reaction is carried out under the conditions (1) and (2), that is, at a concentration of 4 to 10% by weight of nitric acid with a supply of oxygen, a certain measure of improvement is obtained as compared with a conventional process. For instance, glyoxylic acid can be produced in yields of about 80%, and the consumption of nitric acid is decreased to the order of ⅛ to 1/10 time that in a conventional process and nitrogen oxides do not generate in large quantities. However, such a result is not necessarily satisfactory for the industrial manufacture, and the before-mentioned condition (3) is important in practicing the process of the present invention.

A partial pressure of oxygen in the reaction system and a gas-liquid contactor efficiency of an apparatus have a great influence on the yield of glyoxylic acid and consumption of nitric acid. Between the partial pressure of oxygen P (kg./cm.$^2$) and the liquid-phase over-all mass transfer coefficient of the reactor $K_L a$ (1/hour), the relation $K_L a \cdot P \geq 150$ must be set up in the present invention.

The value of the liquid-phase over-all mass transfer coefficient $K_L a$ (1/hour) as used herein shows that determined by a method of air oxidation of sodium sulfite, as described in I.E.C., 36, 504(1944), wherein air is blown through an aqueous solution of sodium sulfite at approximately the same superficial gas velocity as that in practicing the process of the present invention.

In order to satisfy the condition of $K_L a \cdot P \geq 150$, it is required to exactly control the partial pressure of oxygen and the liquid-phase over-all mass transfer coefficient. It is impractical to raise the partial pressure too much, and the above condition is usually satisfied by selecting a reaction apparatus which can provide a high value of $K_L a$. It is absolutely impossible to attain the purpose by such a means as merely bubbling oxygen through a usual reactor equipped with a stirrer, even if its structure is modified or operation conditions are selected. Therefore, it is important to employ an apparatus designed so as to permit efficient gas-liquid contact. As such apparatuses, an agitated gas-liquid reactor and a bubble column are most advantageously employed in the present invention. A packed tower and an ejector may also be employed. In addition, the structure of an agitator, control of the number of revolutions of the agitator, control of the blowing rate of oxygen, control of the quantity of liquid and control of the reaction operation conditions are also important to maintain the condition of $K_L a.P \geq 150$.

When the value of $K_L a.P$ is less than 150, glyoxylic acid cannot be obtained in the desired high yields and also it is difficult to remarkably decrease the consumption of nitric acid and the generation of nitrogen oxides. The larger the value of $K_L a.P$, the more remarkable the effect of the invention. However, it is impractical to raise the value more than 1,000 and the yield is not directly proportional to the value in that region. Therefore, the reaction is practically carried out under conditions of $150 \leq K_L a.P \leq 1,000$, preferably $300 \leq K_L a.P \leq 1,000$.

The reaction is usually carried out at a temperature of 30° to 100° C. In the present invention, it is possible to raise the yield or shorten the reaction time by controlling the reaction temperature in two stages according to the conversion of glyoxal. For instance, the reaction is first carried out at a temperature of 30° to 70° C. until the conversion of glyoxal reaches about 60%. When the reaction temperature is lower than 30° C., the reaction rate is slow and the concentration of nitric acid is required to be high. Also, at a temperature higher than 70° C., there is a possibility of violent reaction or drop of yield. Then, the temperature is elevated within the range not exceeding 100° C. to continue the reaction. By elevating the reaction temperature at the second stage of the reaction, the reaction rate increases and the generation of nitrogen oxides decreases. When elevating the temperature to over 100° C., the produced glyoxylic acid is apt to be converted to oxalic acid and the yield of glyoxylic acid drops. At the second stage, the reaction temperature may be elevated continuously or stepwise at regular intervals, or may be maintained at the prescribed temperature after continuously elevating the temperature.

The initial concentration of glyoxal in the reaction system may be selected in the range of 10 to 50% by weight, preferably 20 to 40% by weight. Glyoxal is generally prepared by oxidizing acetaldehyde with nitric acid in water and is obtained in a form of aqueous solution. Such an oxidation reaction mixture may also be employed after removing acetaldehyde therefrom or treating by an ion-exchange resin or electrodialysis, as well as an aqueous solution of pure glyoxal.

The reaction is usually carried out by adding dropwise nitric acid to an aqueous solution of glyoxal, into which sodium nitrite may be dissolved as occasion demands, while introducing oxygen or an oxygen-containing gas at atmospheric pressure or under pressure. Glyoxal and nitric acid may also be employed in a form of mist which is blown through a reactor to admix with oxygen or an oxygen-containing gas. In the present invention, nitric acid in concentration of 20 to 100% by weight is usually employed. The reaction is usually continued for 3 to 20 hours. The obtained reaction mixture per se, or the reaction mixture from which oxalic acid is separated as crystals, may be used as an aqueous solution of glyoxylic acid in various purposes. In case of containing relatively large quantities of nitric acid or storing for a long period of time, the reaction mixture is purified by a conventional method such as electrodialysis, ion-exchange resin treatment and distillation to prevent the oxidation of glyoxylic acid to oxalic acid. The electrodialysis is suitably adopted in the purification, since it is superior in purification efficiency to other purification means and is industrially advantageous in process steps.

In electrodialysis, the reaction mixture is supplied to an electrodialysis cell where anion-exchange membranes and cation-exchange membranes are alternately arranged. If desired, the reaction mixture may be concentrated prior to the electrodialysis.

The operation of the electrodialysis will be explained particularly with reference to the drawing. The drawing shows one instance of an apparatus employed in the process of the present invention, but the invention is not limited thereto. In the drawing, reference numeral 1 is an electrodialysis cell divided into plural chambers by cation-exchange membranes C and anion-exchange membranes A alternately. One of the end chamber is an anode chamber where the anode (+) is located and the other is a cathode chamber where the cathode (−) is located. The reaction mixture containing glyoxylic acid 2 is supplied to diluent chambers (X1, X2, ... Xn-1 and Xn), and on the other hand, water or nitric acid 3 is supplied to concentrate chambers (Y1, Y2, ... Yn-2 and Yn-1). A direct current is sent between the electrodes, and each of the reaction mixture 2 and the water or nitric acid 3 is continuously passed through each chamber. The treated liquid 4 is an aqueous solution of glyoxylic acid which scarcely contains nitric acid by the selective dialysis action of the ion-exchange membranes. Upon carrying out the electrodialysis, the electric current density is suitably selected from less than 2 A per square decimeter of ion-exchange membrane surface area.

The present invention is more specifically described and explained by means of the following Examples, in which all percents are percent by weight unless otherwise noted.

EXAMPLE 1

An agitated gas-liquid reactor was charged with 100 liters of a 2% aqueous solution of sodium sulfite. Then, air was blown through the reactor at the same superficial gas velocity as that in the practical preparation of glyoxylic acid with stirring the content at 1,000 r.p.m. The consumption rate of sodium sulfite was measured to calculate the over-all mass transfer coefficient of the reactor. The over-all mass transfer coefficient $K_L a$ was 300 (1/hour).

Glyoxylic acid was then prepared by employing the reactor as follows:

The reactor was charged with 71.4 kg. of an aqueous solution of glyoxal containing 35.0% of glyoxal and 3.1% of glyoxylic acid, 13.4 kg. of a 41.0% aqueous solution of nitric acid and 15.2 kg. of water. The temperature was elevated to 60° C. to start the reaction, while the content was stirred at 1,000 r.p.m. and oxygen was blown through the content at 25 liters/min. (at normal temperature and pressure). After the conversion of glyoxal reached 60% by carrying out the reaction at the same temperature for 5 hours, the reaction was further continued with elevating the temperature at uniform velocity to 70° C. over 3 hours. During the reaction, a pressure was applied to the reactor so as to maintain the partial pressure of oxygen inside the reactor at 2.7 kg./cm.$^2$ (absolute pressure) on an average. Also, during the first reaction at 60° C., 3.1 kg. of a 41% aqueous solution of nitric acid was supplied at uniform velocity to maintain the nitric acid concentration of the reaction system at 5 to 7%.

After the completion of the reaction, 108.1 kg. of the reaction mixture was obtained. The reaction mixture contained 24.5% of glyoxylic acid and 4.6% of glyoxal, and the glyoxylic acid yield was 95%. The amount of the consumed nitric acid was 0.030 mole per mole of the consumed glyoxal, and the amount of the formed nitrogen oxides consisting mainly of nitrogen dioxide was 0.0025 mole (calculated as $NO_2$) per mole of the consumed glyoxal.

EXAMPLE 2

An agitated gas-liquid reactor was charged with 100 liters of a 2% aqueous solution of sodium sulfite. Then, air was blown through the reactor at the same superficial gas velocity as that in the practical preparation of glyoxylic acid with stirring the content at 1,200 r.p.m. The consumption rate of sodium sulfite was measured to calculate the over-all mass transfer coefficient of the reactor. The over-all mass transfer coefficient $K_La$ was 410 (1/hour).

Glyoxylic acid was then prepared by employing the reactor as follows:

The reactor was charged with 71.4 kg. of an aqueous solution of glyoxal containing 35.0% of glyoxal and 3.1% of glyoxylic acid, 13.4 kg. of a 41.0% aqueous solution of nitric acid and 15.2 kg. of water. The temperature was elevated to 60° C. to start the reaction, while the content was stirred at 1,200 r.p.m. and air was blown through the content at 100 liters/min. (at normal temperature and pressure). After the conversion of glyoxal reached 60% by carrying out the reaction at the same temperature for 5 hours, the reaction was further continued with elevating the temperature at uniform velocity to 80° C. over 3 hours. During the reaction, a pressure was applied to the reactor so as to maintain the partial pressure of oxygen inside the reactor at 1.5 kg./cm.$^2$ (absolute pressure) on an average. Also, during the first reaction at 60° C., 3.2 kg. of a 41% aqueous solution of nitric acid was supplied at uniform velocity to maintain the nitric acid concentration of the reaction system at 5 to 7%.

After the completion of the reaction, 108.2 kg. of the reaction mixture was obtained. The reaction mixture contained 24.2% of glyoxylic acid and 4.6% of glyoxal, and the glyoxylic acid yield was 94%. The amount of the consumed nitric acid was 0.033 mole per mole of the consumed glyoxal, and the amount of the formed nitrogen oxides was 0.0030 mole (calculated as $NO_2$) per mole of the consumed glyoxal.

EXAMPLE 3

Employing a bubble column, glyoxylic acid was prepared under the condition of $K_La = 200$ (1/hour) as follows:

Amounts of the ingredients charged in the column:
Aqueous solution of glyoxal containing 35.0% of glyoxal and 3.1% of glyoxylic acid: 357 g.
Aqueous solution of nitric acid (41%): 67 g.
Water: 76 g.
Amount of additional aqueous solution of nitric acid (41%): 22 g.
Superficial gas velocity of oxygen: 4 cm./sec.
Amount of oxygen blown: 250 ml./min.
Average partial pressure of oxygen: 2 kg./cm.$^2$
Reaction temperature: 70° to 75° C.
Reaction time: 7 hours
The results were as follows:
Glyoxylic acid yield: 93%
Amount of the consumed nitric acid: 0.040 mole per mole of the consumed glyoxal
Amount of the formed nitrogen oxides: 0.0037 mole (calculated as $NO_2$) per mole of the consumed glyoxal

EXAMPLE 4

An aqueous solution of glyoxylic acid cntaining 24.5% of glyoxylic acid and 4.6% of glyoxal was prepared in the same manner as in Example 1.

Diluent chambers of an electrodialysis apparatus (DU-1 type made by Asahi Glass Co., Ltd.) having 67 diluent chambers and 68 concentrate chambers were charged with 100 kg. of the obtained aqueous solution of glyoxylic acid. Further, concentrate chambers and electrode chambers were charged with 250 kg. of water and 50 kg. of water, respectively. Then, circulation of each liquid was started and a voltage of 60 volts was applied to the electrodialysis cell. The electrodialysis was carried out at the same constant voltage for 6 hours to give 120 kg. of the treated liquid which contained 19.4% of glyoxylic acid, 3.5% of glyoxal and 0.2% of nitric acid. The temperature upon the electrodialysis was 30° to 40° C., and the electric current density was 1 A/dm.$^2$ on an average.

Comparative Example 1

The procedures of Example 1 were repeated except that the reaction was carried out under the condition of $K_La = 50$ instead of $K_La = 300$.

The glyoxylic acid yield was 88%, and the amounts of the consumed nitric acid and the formed nitrogen oxides were 0.050 mole and 0.0047 mole (calculated as $NO_2$), respectively, per mole of the consumed glyoxal.

Comparative Example 2

The procedures of Example 1 were repeated except that oxygen was not supplied.

The glyoxylic acid yield was 64%, and the amounts of the consumed nitric acid and the formed nitrogen oxides consisting mainly of nitrogen monoxide were 0.74 mole and 0.24 mole (calculated as NO), respectively, per mole of the consumed glyoxal.

What we claim is:

1. In a process for preparing glyoxylic acid by oxidizing glyoxal with nitric acid at an elevated temperature of 30–100° C., the improvement comprising
    1. maintaining the concentration of nitric acid at 4 to 10% by weight based on the total weight of the reaction system,
    2. introducing oxygen or an oxygen-containing gas into the reaction system, and
    3. maintaining the relationship of the reaction system: $K_La \cdot P \geq 150$,
    wherein $K_La$ is a liquid-phase over-all mass transfer coefficient (1/hour) and
    P is a partial pressure of oxygen in the reaction system (kg/cm$^2$).

2. The process of claim 1, wherein said oxygen or oxygen-containing gas is continuously introduced into the reaction system.

3. The process of claim 1, wherein said oxygen or oxygen-containing gas is introduced at intervals into the reaction system.

4. The process of claim 1, wherein said concentration of nitric acid is maintained at 5 to 8% by weight based on the total weight of the reaction system.

5. The process of claim 1, wherein said relationship satisfies a relation $150 \leq K_La \cdot P \leq 1,000$.

* * * * *